United States Patent [19]

Weber

[11] Patent Number: 4,773,854

[45] Date of Patent: Sep. 27, 1988

[54] DEVICE FOR THE REPRESENTATION AND CORRECTION OF CONDYLAR MOTIONS

[76] Inventor: Roland Weber, Grand-Chene 5, CH-1003 Lausanne, Switzerland

[21] Appl. No.: 690,247

[22] Filed: Jan. 10, 1985

Related U.S. Application Data

[63] Continuation of PCT CH84/00071 filed on May 10, 1984.

[30] Foreign Application Priority Data

May 10, 1983 [CH] Switzerland .......................... 2549/83

[51] Int. Cl.$^4$ ............................................. A61C 11/00
[52] U.S. Cl. ....................................... 433/57; 433/69; 433/73
[58] Field of Search ....................... 433/57, 61, 62, 64, 433/68, 69, 73

[56] References Cited

U.S. PATENT DOCUMENTS

| 2,070,025 | 2/1937 | Phillips | 433/64 |
| 3,431,649 | 3/1969 | Guichet | 433/73 |
| 3,552,020 | 1/1971 | Weber | 433/57 |
| 4,058,895 | 11/1977 | Mack et al. | 433/57 |
| 4,185,387 | 1/1980 | Weber | 433/61 |
| 4,290,754 | 9/1981 | Edwardson | 433/57 |

Primary Examiner—John J. Wilson
Attorney, Agent, or Firm—Sherman and Shalloway

[57] ABSTRACT

Disclosed herein is a device for the representation of condylar movements of a patient and their correct simulation which includes models of sets of teeth to determine the required corrections to the biting surfaces in order to obtain ideal occlusion. The device includes an articulator with the lower part thereof able to be brought into a predetermined three-dimensional relation with respect to an upper part of the articulator and having two blocks having guide elements on the lower part of the articulator to support condyle balls of the upper part of the articulator. The device further includes a lower jaw recording bow and an upper jaw recording bow which can be brought into an active and predetermined relation with respect to the articulator and which disposes of at least three recording plates with corresponding recording pins as well as positioning spoons for the combination of a lower jaw dentition model. With this device, opening movements of articulation may be recorded three-dimensionally so that three clear crossing points are created for the occlusion.

7 Claims, 3 Drawing Sheets

DEVICE FOR THE REPRESENTATION AND CORRECTION OF CONDYLAR MOTIONS

This application is a continuation of international application PCT/CH84/00071, filed in the Swiss Patent Office on May 10, 1984.

BACKGROUND OF THE INVENTION

The present invention concerns an improved device for representation of condylar motions of a patient and their correct simulation, including models of sets of teeth, to determine the required corrections to the biting surfaces in order to obtain an ideal occlusion.

In dental therapeutics, numerous models and devices are known—for example out of the 1961 by Mosby & Co published volume "Modern Gnathological Concepts" written by Victor O. Lucia—which serve the purpose of representation and reproduction of a patient's habitual occlusion and shall correct the patient's functional and occlusional disturbances by correcting the biting surfaces profiles of the teeth on the upper and the lower jaw. But the therapist knows that all those models and devices either are very complicated to operate and/or produce results of which the practical analysis is very consuming. In addition to that, ordinarily no subsequent correction to the positioning of the biting surfaces of the upper and the lower jaw teeth can be made on the model in order to balance out mounting errors or expansion errors of plaster. Further, often separate devices are used for representation on condylar motions of a patient and their reproduction, which makes the reproducibility of measurements and motions uncertain, if not even impossible.

These disadvantages have largely been eliminated by Weber's developed articulator according to CH-PS No. 437 629 (U.S. Pat. No. 3,552,020) as well as his further development according to CH Pat. No. 604 675 (U.S. Pat. No. 4,185,387). This device allows for the first time to adjust the three-dimensional relation between the lower jaw and the upper jaw and the movements of the lower jaw with an appropriate recording of the marginal movements, which is achieved by a pertinent pantograph in connection with an adjustable control foot. With these known devices by Weber, for the first time the whole set of problems around the "centric registry" can be solved satisfactorily.

SUMMARY OF THE INVENTION

The task of the present invention is to create a further improved device which offers more extended possibilities in comparison to Weber's known device on one hand and a more simplified manipulation on the other hand.

According to the invention, the improved device solves this task as defined in claims 1.

BRIEF DESCRIPTION OF THE DRAWINGS

In the following the drawing describes an advantageous version of embodiment of the device according to the invention as well as its application. In that drawing

Figure 1:
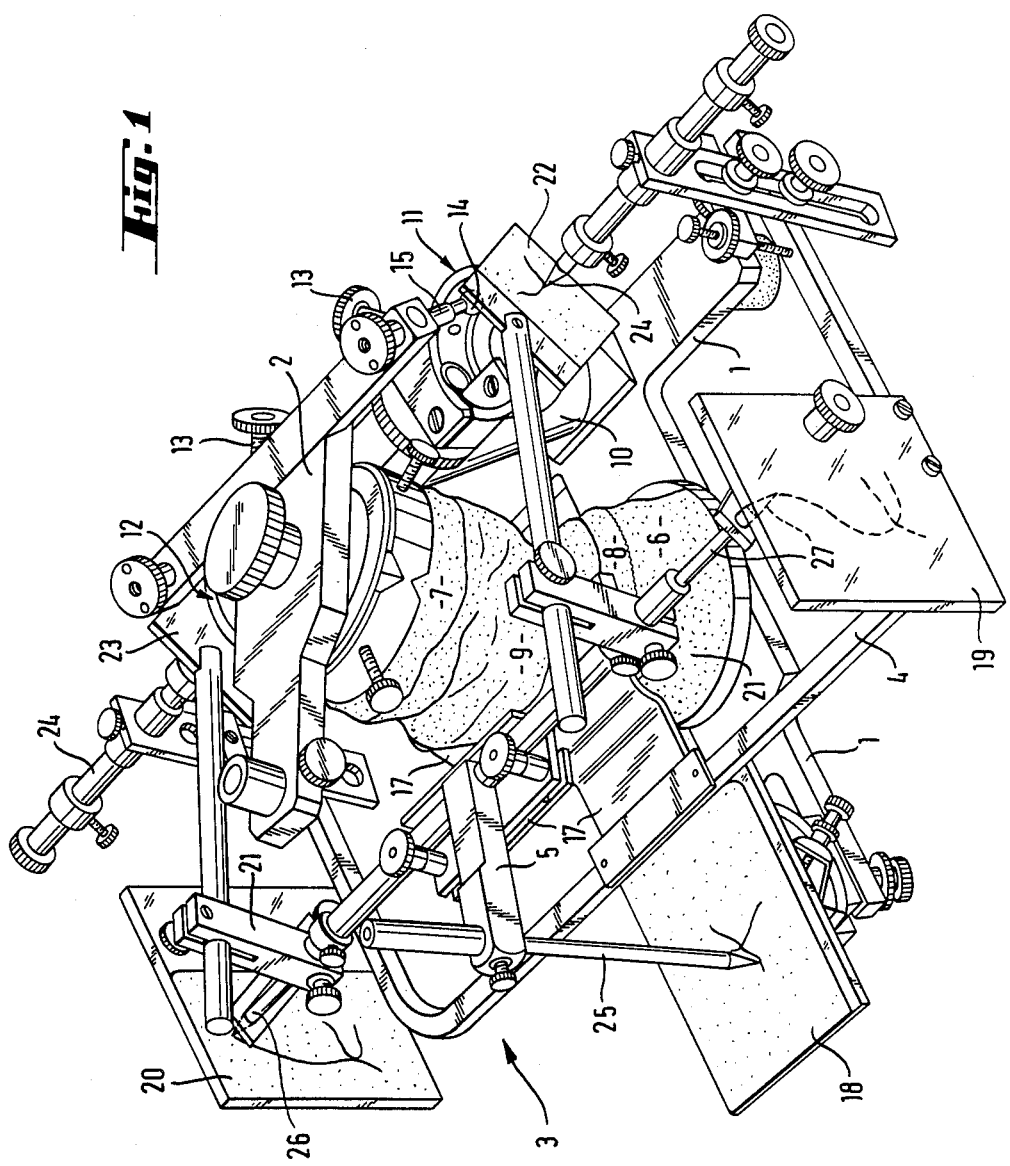
FIG. 1 shows the device in the combination which is used for the reproduction of the lower jaw movements recorded on the patient with plaster casts of the patient's upper jaw and lower jaw.
Figure 2:
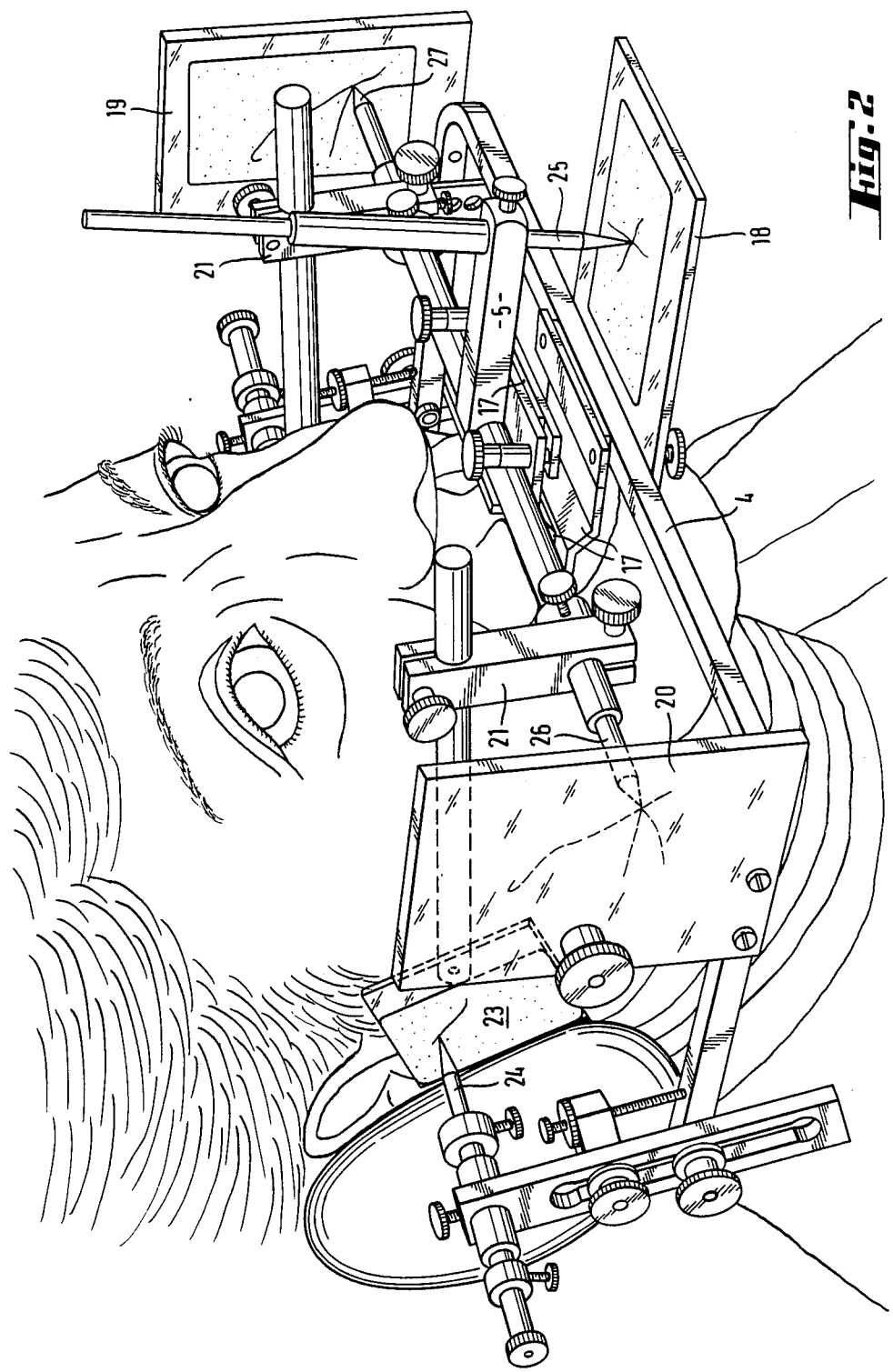
FIG. 2 shows the pantograph part in operation of recording of the habitual occlusion of a female patient.

The drawing as well as the description do not describe in detail all the parts already mentioned in other patent claims or publications which have been pointed out separately, as those parts and their application probably are known to every expert. In order to avoid repetitions and to simplify the characteristics of the device according to the invention in comparison to the well known devices by Weber, these articulators are always compared together in the following.

SPECIFIC DESCRIPTION OF THE PREFERRED EMBODIMENT

In FIG. 1, one can recognize the single parts of the device according to the invention, which mainly are the lower part of the articulator 1, the upper part of the articulator 2, which is pivotably mountable, as well as a pantograph part 3, consisting of a lower jaw recording bow 4 and an upper jaw recording bow 5. Every part of 1 and 2 carries a dentition model: the lower part of the articulator 1 the lower jaw dentition model 6 and the upper part of the articulator 2 the upper jaw dentition model 7. In addition to that, the lower jaw recording bow 4 carries the lower jaw dentition model 8 and the upper jaw recording bow 5 carries the upper jaw dentition model 9. It is of advantage that both models 6 and 7 are connected to the pertinent articulator parts as described in CH-PS No. 604 675 and the models 8 and 9 are attached to the corresponding recording bows with intraoral positioning spoons according to the international model DM/001 188.

Figure 3:
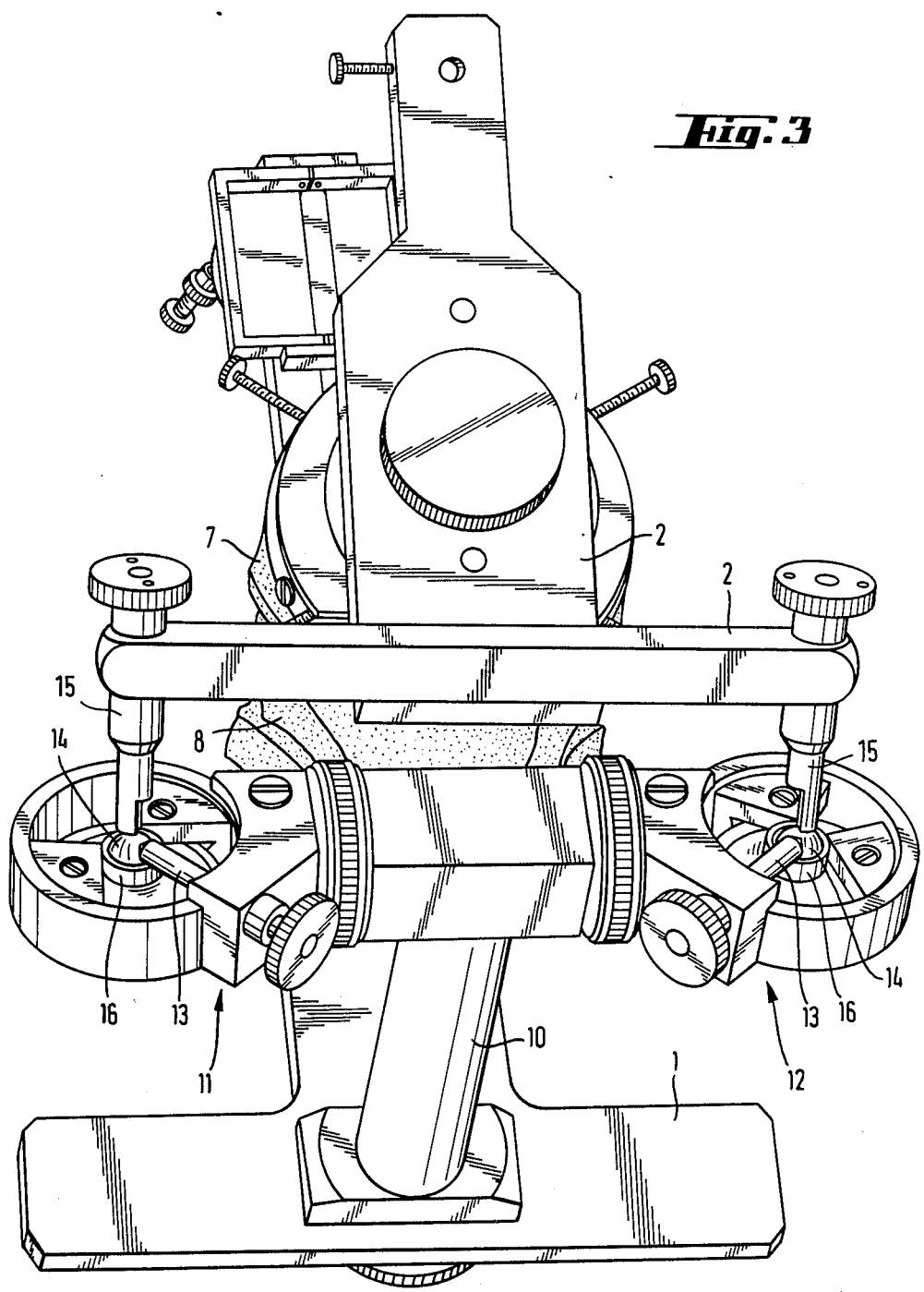
FIG. 3 is a backview from the top of the articulator part of the device and shows the mounting of the blocks of guide elements with which the upper part of the articulator is positioned on the lower part.

Compared to the well known models of articulators by Weber, the single parts of the new device mainly differ by the following characteristics:

The lower part of the articulator 1:
only disposes of one middle support 10 (FIG. 3), so that the diagonal view on the models mounted on the articulator is granted and all teeth are accessible.

Both blocks 11 and 12 (FIG. 3) of the guide elements are mounted on a common central axis, the intercondyle axis, and not on two separate lateral devices anymore. Consequently they are fixed together in their relative position and pivotable around the intercondyle axis.

Every block 11/12 is laterally movable on the intercondyle axis and each disposes of a screw cylinder pin 13, with which the condyle balls 14 (FIG. 3) can be fixed.

It disposes of an already known movable support for a front support pin in its central front part.

The upper part of the articulator 2:
can hold in the front part a movable and lockable front support pin.

The arms 15 with the condyle balls 14 placed at the lower ends are equiped with accessory rings 16 which can be shifted over the balls 14 and increase their effective diametrical plane. So the retrusion movements of a diagnosis of transversal and retral deplacements due to occlusion can be simulated without losing the mounting position of the models. The arms are also fixed and therefore not movable laterally.

The lower jaw recording bow 4 is mainly unchanged, but:

the ball heads, that had to be adjusted on the intercondyle axis of the lower jaw and were mounted on U-shaped legs, are now replaced by bars 24 that can be put into the intercondyle axis, the lower jaw dentition model 8 is connected to the lower jaw recording bow by the before described positioning spoon 17. That spoon disposes in its turn of a Mc Grane pin that can be positioned.

the front recording plate 18 as well as the two lateral recording plates 19 and 20 consist of plexiglass and are removable. All three plates 18 to 20 can be positioned reproducibly. The lateral recording plates 19 and 20 are adjusted and staggered, so that the opening movements can also be recorded fully three-dimensionally.

The upper jaw recording bow 5 differs from the already known one by the fact:

that it carries the upper jaw dentition model 9 on a removable positioning spoon 17 that has been mentioned before, but without the Mc Grane pin, that accessory recording plates 22 and 23 are mounted with clamped on supports 21, so that they can co-operate with the points 24. Those additional sagittal-vertical recording plates improve the diagnostic possibilities by reproducing directly pathological changements of the condylar movements as well as misfunctions of the discus cartilagis. With that, the basic requirements for a derivation of the so-called "therapeutic centricity" is met, that the Mc Grane support pin is guided on the positioning spoon that serves as guide plate in such a way that three clear crossing points are created for the centricity with the recording of all articulation movements on the recording planes, arranged in an especially constructed position.

The expert recognizes that with all these modifications the well known articulator models by Weber—as Stachniss states in his habilitation they are the only devices of this kind with which the three-dimensional relation between the lower jaw and the upper jaw is adjustable by recording the marginal movements and therefore the problems of the correctly reproducible "centric registry", that hardly can be solved, are avoidable—have been improved considerably in certain and important respects. Consequently, fundamental disadvantages of these known devices could be eliminated and new possibilites created.

Before all, the new design of the lower part of the articulator 1 presents essential advantages in comparison to all known articulators, as the only middle support 10 allows free access to all teeth of the model. In addition, the firm combination of the blocks 11 and 12 on the intercondyle axis as support of the upper part of the articulator 2, connected to the cylinder pins 13 with which the condyle balls 14 can be fixed on the guide elements, offers for the first time the possibility of folding down the upper part of the articulator 2, without losing its relative position to it.

Further it is possible for the first time to realize every desired therapeutic front, rear and side bite position of the models 6/7 without adjustment, because of the pregressive side-shift of each block 11/12 on the intercondyle axis and the application of the accessory rings 16.

Those possibilities can be extended additionally by the application of curve disk inserts as supports for the condyle balls 14 in the blocks 11 and 12.

With a side bite positioning unit, arranged centricly and movably around each block, consisting mainly of a locking screw that can operate on the condyle balls (14), every side bite position of the models 6,7, respectively all mediotrusion and laterotrusion movements in the articulator can be positioned.

The new device offers for the first time the possibility of a direct and simultaneous combination of the determination of the axis and the recording of the condyle movements in one single working process. In addition, it renders possible to record the precise movements of the jaw joint on the intercondyle axis as well as locally and chronologically accurately every pathological cracking of the jaw joint with the accessory recording plates 22 and the points 24.

Thanks to the locally precise reproduction of the positioning of all recording plates (18,19,20 and 22, 23) and the models 8,9 of the pantograph part 3 as well as the dentition models 6,7 on the articulator, and the fact that it can be reinserted into the patient's mouth for control of the work at any time and without having to change any adjustment on it or on the articulators 1,2, it is possible to reproduce at any moment the habitual and the ideal occlusion of a patient, even if all parts have been disassembled. For the first time a transfer of the results and measured values from one device to another can take place without any problems. With the device according to the invention it is also possible to record computer-conform and to analyse all measured values and articulation movements by converting them into electric signals with any known method.

The articulators 1,2 can be used as movable and three-dimensional reproduction of a patient's set of teeth or as pure joint, without having to change any adjustments or measured values, as the common axis of the two blocks 11, 12 is positioned on ball bearings and can be locked in a defined position in relation to the firm middle support 10, or positioned freely pivotably around its longitudinal axis, the condyle axis, whereas the relative position of the two blocks 11, 12 always remains firm and reproducible to each other and the upper part of the articulator 2 can also be firmly positioned and reproduced in relation to the blocks 11, 12, because of its screw cylinder pins 13. This simplifies considerably the work of grind-in of correct biting surfaces on the models, as the upper part of the articulator 2 can be folded back into a completely stable horizontal position, parallel to the lower part, by screwing down the cylinder pins 13 and setting free the axis of the condyle axis, without having to prop it backwards on the inserted and locked frontal support pin. Now one can work on the lower jaw model as well as on the upper jaw model without any problems, whereas the original three-dimensional relation between the lower jaw model and the upper jaw model can be reinstalled by the simple folding back of the upper jaw part 2 and the blocking of the mentioned axis as well as the unscrewing of the cylinder pins.

The expert will notice immediately how important the above mentioned improvements are and how the application of the new device, that inevitably consists of the articulator parts 1, 2 and the pantograph part 3, simplifies his work.

The above described improved device for the representation of condylar movements of a patient and their correct simulation can be adapted and/or further improved in detail if necessary. So all recording plates can for instance be provided with positioning and fastening elements—for example in form of adjustable clamping bars and positioning pins—for the reproducible positioning of not self-adhesive recording paper. In addition, the recording plates can be furnished with transparent cover sheets that prevent the recording paper from undesired marks on the curves recorded at the reproduction.

Further, the recording points can end in miniature balls or be replaced by self-recording pins, if not recording paper shall be used that is pressure sensitive. In order to facilitate the removing of the plaster foot from the articulator, it can be provided with a hydrophobic permanent layer.

The front support pin can be clamped in a guide slot or mounted on a movable slide, so that it can be fixed pivotably and tiltably in every front bite and rear bite position. Through that, the immediate side-shift can be reproduced correctly at the back. In order to render the respective position of the pin determinable, an adjustment scale can be worked out.

I claim:

1. Improved device for the representation of condylar movements of a patient and their correct simulation, including models of sets of teeth to determine the required corrections to the biting surfaces in order to obtain an ideal occlusion, which mainly consists of an articulator (1) with the lower part of the articulator (1) that can be brought in a predetermined three-dimensional relation to the upper part of the articulator (2), with two blocks (11, 12) with guide elements on the lower part of the articulator (1) for the support of the condyle balls (14) of the upper part of the articulator (2) and means for the defined and reproducible mounting of the lower jaw dentition model and the upper jaw dentition model (6, 7) as well as a pantograph part (3) removably connected to said articulator and consisting of a lower jaw recording bow (4) and an upper jaw recording bow (5) that can be brought in an active and predetermined relation to the articulator (1) and disposes of at least three recording plates (18, 19, 20) with the corresponding recording pins (25, 26, 27) as well as positioning spoons (17) for the combination of a lower jaw dentition model (8) with the lower jaw recording bow (4) and an upper jaw dentition model (9) with the upper jaw recording bow (5), that characterize the whole device with three recording plates in co-operation with the Mc Grane support pin, arranged on an especially formed guide plane in a certain distance and position, that the opening movements of the articulation are recorded fully three-dimensionally, so that three clear crossing points are created for the occlusion and that the lower part of the articulator (1) disposes of a single middle support (10), which carries the two blocks (11, 12) of the guide elements on a common axis, whereas the upper part can always be folded back freely and stably, parallel to the lower part.

2. Device according to claim 1, characterized by the fact that the mentioned axis is positioned in two ball bearings and can be locked reproducibly with a positioning screw in a pre-determined position.

3. Device according to any one of claim 1 or 2, characterized by the fact that the upper part of the articulator remains stable in the horizontal position when folded back, without needing a support pin.

4. Device according to any one of claim 1 or 2, characterized by the fact that the articulator disposes of a frontal support pin, which can be locked pivotably in a sagittal guidance in every desired position.

5. Device according to claim 1, characterized by the fact that the guide elements are removable and allow a programmed side-shift movement as well as a retral movement and with that the imitation of every habitual position, without having to change the position of the models.

6. Device according to any one of claims 1, 2, or 5, characterized by the fact that the articulator disposes of a frontal support pin, which can be locked pivotably and universally tiltably in a sagittal guidance in every desired position.

7. Device according to claim 1, characterized by the fact that every condyle ball is positioned with a respective guide element whereas the balls can be fixed with a centering screw, pointing centrally at the ball supports, so that they can be screwed in the guide bearing free from play and centrally pivotably.

* * * * *

UNITED STATES PATENT AND TRADEMARK OFFICE
CERTIFICATE OF CORRECTION

PATENT NO. : 4,773,854
DATED : September 27, 1988
INVENTOR(S) : ROLAND WEBER

It is certified that error appears in the above-identified patent and that said Letters Patent is hereby corrected as shown below:

On the face of the patent, under "Foreign Application Priority Data", the application number for the Switzerland application should be changed from " 2549/83 " to read -- 2549/83-9 --.

Signed and Sealed this

Fourteenth Day of February, 1989

Attest:

DONALD J. QUIGG

*Attesting Officer*  *Commissioner of Patents and Trademarks*